(12) United States Patent
Dorey et al.

(10) Patent No.: US 9,462,082 B2
(45) Date of Patent: Oct. 4, 2016

(54) MEDIA ACQUISITION ENGINE AND METHOD

(75) Inventors: Matthew Dorey, San Francisco, CA (US); George Stantchev, Phoenix, AZ (US); Marwan Hilmi, Beaconsfield (CA); Richard Compton, Calgary (CA); Case Nelson, Calgary (CA); Shaun Kaasten, Toronto (CA)

(73) Assignee: Curve Dental Ltd., Calgary (CA)

( * ) Notice: Subject to any disclaimer, the term of this patent is extended or adjusted under 35 U.S.C. 154(b) by 749 days.

(21) Appl. No.: 13/570,532

(22) Filed: Aug. 9, 2012
(Under 37 CFR 1.47)

(65) Prior Publication Data

US 2013/0226993 A1  Aug. 29, 2013

Related U.S. Application Data

(60) Provisional application No. 61/522,650, filed on Aug. 11, 2011.

(51) Int. Cl.
*G06F 15/16* (2006.01)
*H04L 29/06* (2006.01)
*H04L 29/08* (2006.01)
*G06F 17/30* (2006.01)

(52) U.S. Cl.
CPC ......... *H04L 67/42* (2013.01); *G06F 17/30861* (2013.01); *H04L 67/10* (2013.01)

(58) Field of Classification Search
CPC ...................................................... H04L 67/42
USPC ............................................ 709/203; 725/61
See application file for complete search history.

(56) References Cited

U.S. PATENT DOCUMENTS

| | | | |
|---|---|---|---|
| 2005/0278748 A1* | 12/2005 | Koh et al. ...................... | 725/61 |
| 2006/0036625 A1* | 2/2006 | Judd et al. ..................... | 707/100 |
| 2009/0210032 A1* | 8/2009 | Beiski et al. .................. | 607/59 |
| 2012/0284657 A1* | 11/2012 | Hafey et al. ................... | 715/765 |
| 2013/0129165 A1* | 5/2013 | Dekel et al. ................... | 382/128 |

* cited by examiner

*Primary Examiner* — David Lazaro
*Assistant Examiner* — Marie Georges Henry
(74) *Attorney, Agent, or Firm* — Sheppard, Mullin, Richter & Hampton LLP

(57) ABSTRACT

Disclosed is a media acquisition engine that comprises an interface engine that receives a selection from a plug-in coupled to a media client engine where a client associated with the media client engine identified as subscribing to a cloud application imaging service. The media acquisition engine further comprises a media control engine that directs, in accordance with the selection, a physical device to image a physical object and produce a media item based on the image of the physical object, the physical device being coupled to a cloud client. The media acquisition engine also comprises a media reception engine that receives the media item from the physical device, and a translation engine that encodes the media item into a data structure compatible with the cloud application imaging service. The interface engine is configured to transfer the media item to the plug-in.

20 Claims, 9 Drawing Sheets

MEDIA ACQUISITION ENGINE AND METHOD

CROSS-REFERENCE TO RELATED APPLICATIONS

This application claims priority to U.S. Provisional Patent Application No. 61/522,650, filed Aug. 11, 2011, entitled "MEDIA ACQUISITION ENGINE AND METHOD," which is incorporated herein by reference in its entirety.

BACKGROUND

Digital imaging has notable advantages over traditional imaging, which processes an image of a physical object onto a physical medium. Digital imaging help users such as health professionals avoid the costs of expensive processing equipment, physical paper, physical radiographs, and physical film. Techniques such as digital radiography expose patients to lower doses of radiation than traditional radiography and are often safer than their traditional counterparts are. Moreover, digital images are easy to store on storage such as a computer's hard drive or a flash memory card, are easy transferable, and are more portable than traditional physical images. Further, many digital imaging devices use sophisticated image manipulation techniques and filters that accurately image physical objects. A health professional's information infrastructures and the business processes can therefore potentially benefit from digital imaging techniques.

Though digital imaging has many advantages over physical imaging, digital imaging technologies are far from ubiquitous in health offices as existing digital imaging technologies present their own costs. To use existing digital imaging technologies, a user such as a health professional has to purchase separate computer terminals and software licenses for each treatment room. As existing technologies install a full digital imaging package on each computer terminal, these technologies are often expensive and present users with more options than they are willing to pay for. Additionally, existing digital imaging technologies require users to purchase a complete network infrastructure to support separate medical imaging terminals. Users often face the prospects of ensuring software installed at separate terminals maintains patient confidentiality, accurately stores and backs up data, accurately upgrades, and correctly performs maintenance tasks. As such, existing digital imaging technologies are not readily compatible with the objectives of end-users, such as health professionals.

The foregoing examples of the related art and limitations related therewith are illustrative and not exclusive. Other limitations of the related art will become apparent upon a reading of the specification and a study of the drawings.

SUMMARY

Various technologies reduce or eliminate one or more of the above-described problems, while other examples target other improvements. The following examples and aspects thereof are described and illustrated in conjunction with systems, tools, and methods that are illustrative, but not necessarily limiting in scope.

A media acquisition engine can take the form of an engine inside a client system on a network. The network can have a cloud-based architecture in which a shared pool of configurable resources is located at one or more locations in the network. The media acquisition engine can comprise an interface engine that receives a plug-in that is coupled to a media client engine, also within the client system. A client that is associated with the media client engine may or may not subscribe to a cloud application imaging service.

The media acquisition engine can include a media control engine that directs, in accordance with the selection from the plug-in, one of a plurality of physical devices to image a physical object and produce a media item based on the image of the physical object. The client system can receive by coupling the one of the plurality of physical devices.

The media acquisition engine may or may not include an interface engine that transfers the encoded media item to the media client engine in addition to the plug-in. The media control engine of the media acquisition engine can direct the one of the plurality of physical devices by communicating with a device driver related to the one physical device.

The media acquisition engine can comprise other engines, such as a media reception engine and a translation engine, which can encrypt the media item. The interface engine can transfer the media item to the plug-in and/or the media client engine.

The media acquisition engine can accept user input or run on scripts executed on the media client engine. A media filtering engine can filter the media item to ensure the media item meets basic quality control standards, including minimum or user-defined resolutions and/or image standards.

The plurality of physical devices can include one or more devices that include sensor-based imaging technologies. The sensor-based imaging technology can include an oral sensor, a digital radiography device, a thermal-based imaging technology, and/or a dental imaging technology, among other technologies.

This application also discloses a method related to the media acquisition engine. The method can include: receiving a selection from a media client engine, a client associated with the media client engine identified as subscribing to a cloud application imaging service; directing, in accordance with the selection, one of a plurality of physical devices to image a physical object and produce a media item based on an image of the physical object; receiving the media item from the one of the plurality of physical objects; encoding the media item into a data structure compatible with the cloud application imaging service; and transferring the encoded media item to the media client engine.

DETAILED DESCRIPTION OF THE INVENTION

The following description presents specific details to provide a thorough understanding. One skilled in the relevant art will recognize, however, that the concepts and techniques disclosed herein can be practiced without one or more of the specific details, or in combination with other components, etc. In other instances, the following description does not show or describe in detail well-known implementations or operations to avoid obscuring aspects of various examples disclosed.

Figure 1:
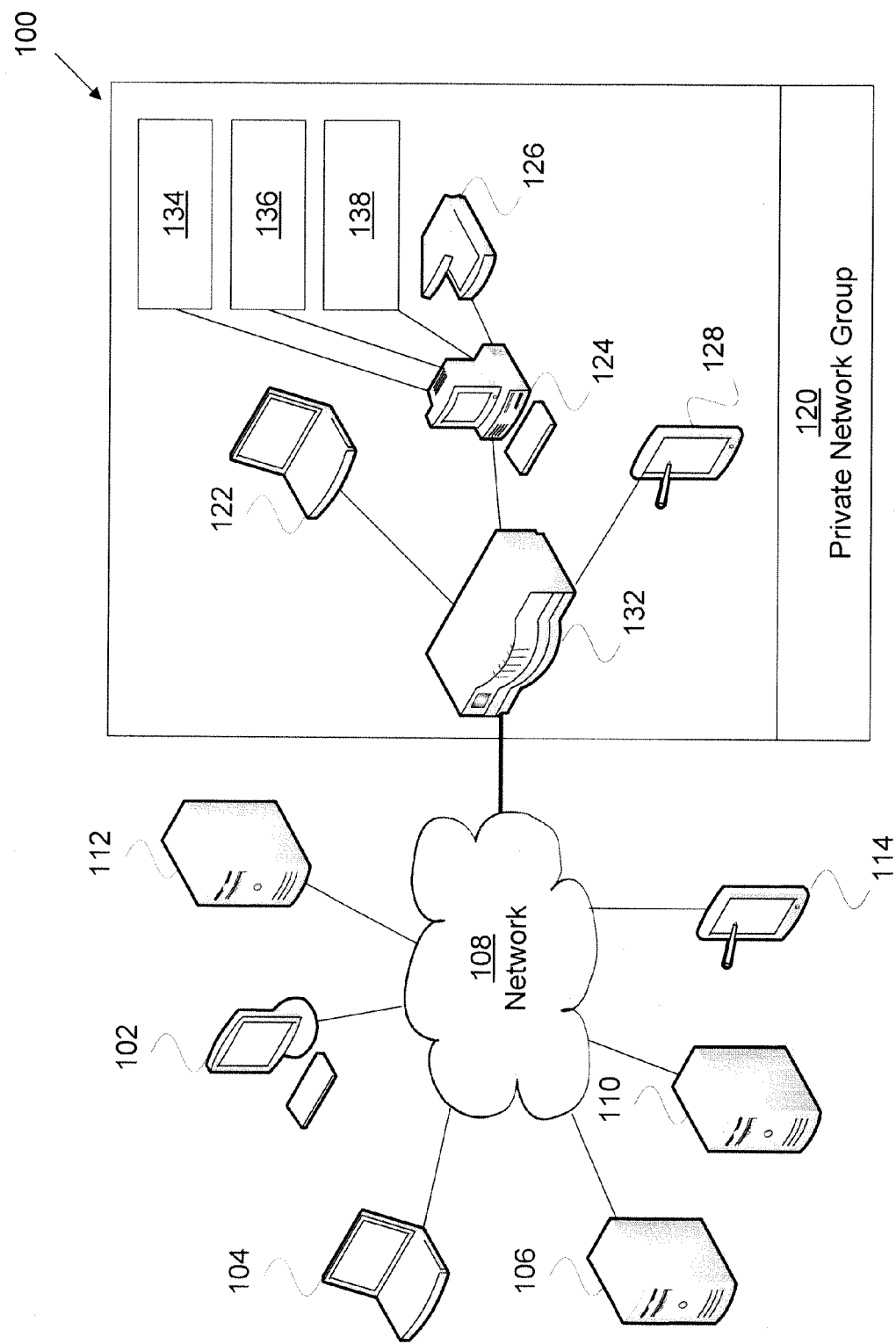
FIG. 1 shows a conceptual diagram of an example of a networking system.

FIG. 1 shows a conceptual diagram of an example of a networking system 100 for providing one or more application imaging services. The networking system 100 comprises by way of example but not limitation, a desktop computer 102, a laptop computer 104, a server 106, a network 108, a server 110, a server 112, a tablet device 114, and a private network group 120. The private network group 120 comprises by way of example but not limitation a laptop computer 122, a desktop computer 124, a scanner 126, a tablet device 128, an access gateway 132, a first physical device 134, a second physical device 136, and a third physical device 138. As will be discussed with reference to FIGS. 8 and 9, the networking system 100 can incorporate devices similar to the devices shown in FIGS. 8 and 9.

The desktop computer 102, the laptop computer 104, the server 106, the server 110, the server 112, and the tablet device 114 are shown directly connected to the network 108, but can be grouped in a manner similar to the private network group 120 without departing from the scope and substance of the inventive concepts disclosed herein. The desktop computer 102 can include a computer having a separate keyboard, monitor, and processing unit. The desktop computer 102 can integrate one or more of the keyboard, the monitor, and the processing unit into a common physical module. The laptop computer 104 can include a portable computer. The laptop 104 can integrate the keyboard, monitor, and processing unit into one physical module. The laptop 104 can also have a battery so that the laptop 104 allows portable data processing and portable access to the network 108. The tablet 114 can include a portable device with a touch screen, a monitor, and a processing unit all integrated into one physical module.

Any or all of the computer 102, the laptop 104, and the tablet device 118 can include a computer system. A computer system will usually include a processor, memory, non-volatile storage, and an interface. Peripheral devices can also form a part of the computer system. A typical computer system will include at least a processor, memory, and a device (e.g., a bus) coupling the memory to the processor. The processor can include, for example, a general-purpose central processing unit (CPU), such as a microprocessor, or a special-purpose processor, such as a microcontroller. The memory can include, by way of example but not limitation, random access memory (RAM), such as dynamic RAM (DRAM) and static RAM (SRAM). The memory can be local, remote, or distributed. The term "computer-readable storage medium" includes physical media, such as memory.

The bus of the computer system can couple the processor to non-volatile storage. The non-volatile storage is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. A direct memory access process often writes some of this data into memory during execution of software on the computer system. The non-volatile storage can be local, remote, or distributed. The non-volatile storage is optional because systems need only have all applicable data available in memory.

Software is typically stored in the non-volatile storage. Indeed, for large programs, it may not even be possible to store the entire program in memory. Nevertheless, for software to run, if necessary, it is moved to a computer-readable location appropriate for processing, and for illustrative purposes, this paper refers to that location as the memory. Even when software is moved to the memory for execution, the processor will typically make use of hardware registers to store values associated with the software, and local cache that, ideally, serves to speed up execution. As used herein, a software program is assumed to be stored at any known or convenient location (from non-volatile storage to hardware registers) when the software program is referred to as "implemented in a computer-readable storage medium." A processor is "configured to execute a program" when at least one value associated with the program is stored in a register readable by the processor.

The bus can also couple the processor to one or more interfaces. The interface can include one or more of a modem or network interface. A modem or network interface can be part of the computer system. The interface can include an analog modem, isdn modem, cable modem, token ring interface, satellite transmission interface (e.g. "direct PC"), or other interfaces for coupling a computer system to other computer systems. The interface can include one or more input and/or output (I/O) devices. The I/O devices can include, by way of example but not limitation, a keyboard, a mouse or other pointing device, disk drives, printers, a scanner, and other I/O devices, including a display device. The display device can include, by way of example but not limitation, a cathode ray tube (CRT), liquid crystal display (LCD), or some other applicable known or convenient display device.

In one example of operation, operating system software that includes a file management system, such as a disk operating system, can control the computer system. One example of operating system software with associated file management system software is the family of operating systems known as Windows® from Microsoft Corporation of Redmond, Wash., and their associated file management systems. Another example of operating system software with its associated file management system software is the Linux operating system and its associated file management system. The file management system is typically stored in the non-volatile storage and causes the processor to execute the various acts required by the operating system to input and output data and to store data in the memory, including storing files on the non-volatile storage.

Some portions of the detailed description refer to algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The algorithms and displays presented herein do not inherently relate to any particular computer or other apparatus. Various general-purpose systems can be used with programs to configure the general-purpose systems in a specific manner in accordance with the teachings herein as specifically purposed computer systems, or it can prove convenient to construct specialized apparatus to perform the methods of some embodiments. The required structure for a variety of these systems will appear from the description below. In addition, though portions of the description relate to specific programming languages and/or standards, various embodiments use a variety of programming languages for implementation.

Any or all of the computer 102, the laptop 104, and the tablet device 118 can include engines. As used in this paper, an engine includes a dedicated or shared processor and, typically, firmware or software modules that the processor executes. Depending upon implementation-specific or other considerations, an engine can have a centralized distributed location and/or functionality. An engine can include special purpose hardware, firmware, or software embodied in a computer-readable medium for execution by the processor. As used in this paper, a computer-readable medium is intended to include all mediums that are statutory (e.g., in the United States, under 35 U.S.C. 101), and to specifically exclude all mediums that are non-statutory in nature to the extent that the exclusion is necessary for a claim that includes the computer-readable medium to be valid. Known statutory computer-readable mediums include hardware (e.g., registers, random access memory (RAM), non-volatile (NV) storage, to name a few), but may or may not be limited to hardware.

Any or all of the computer 102, the laptop 104, and the tablet device 118 can include one or more datastores. A datastore can be implemented, for example, as software embodied in a physical computer-readable medium on a general- or specific-purpose machine, in firmware, in hardware, in a combination thereof, or in an applicable known or convenient device or system. Datastores in this paper are intended to include any organization of data, including tables, comma-separated values (CSV) files, traditional databases (e.g., SQL), or other applicable known or convenient organizational formats. Datastore-associated components, such as database interfaces, can be considered "part of" a datastore, part of some other system component, or a combination thereof, though the physical location and other characteristics of datastore-associated components is not critical for an understanding of the techniques described in this paper.

Datastores can include data structures. A data structure is associated with a particular way of storing and organizing data in a computer so for efficient use within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. Any or all of the computer 102, the laptop 104, and the tablet device 118 can include hardware and/or software components similar to the components shown in the computer system of FIG. 9.

The desktop computer 102, the laptop 104, or the tablet device 114 can function as network clients. Any or all of the desktop computer 102, the laptop 104, and the tablet device 114 can include one or more operating system software as well as application system software. For instance, the desktop computer 102, the laptop 104, or the tablet device 114 can run a version of a Windows® operating system from Microsoft Corporation, a version of a Mac operating system from Apple Corporation, a Linux based operating system such as an Android operating system, a Symbian operating system, a Blackberry operating system, or other operating system. The desktop computer 102, the laptop 104, and the tablet device 114 can also run one or more applications with which end-users can interact. For instance, the desktop computer 102, the laptop 104, and the tablet device 114 can run word processing applications, spreadsheet applications, imaging applications, and other applications. Any or all of the desktop computer 102, the laptop 104, and the tablet device 114 can also run one or more programs that allow a user to access content over the network 108. For instance, any or all of the desktop computer 102, the laptop 104, and the tablet device 114 can include one or more web browsers that access information over the network 108 by Hypertext Transfer Protocol (HTTP). The desktop computer 102, the laptop 104, and the tablet device 114 can also include applications that access content via File Transfer Protocols (FTP) or other standards.

In some embodiments, the desktop computer 102, the laptop 104, or the tablet device 114 can also function as servers. A server is an electronic device that includes one or more engines dedicated in whole or in part to serving the needs or requests of other programs and/or devices. The discussion of the servers 106, 110, and 112 provides further details of servers. Moreover, as discussed below, the desktop computer 102, the laptop 104, or the tablet device 114 can distribute data and/or processing functionality across the network 108 to facilitate providing cloud application imaging services. Thus, as discussed below, any of the desktop computer 102, the laptop 104, and the tablet device 114 can incorporate modules such as the cloud-based server engine 200, shown in FIG. 2

Any of the server 106, the server 110, and the server 112 can comprise computer systems. Any of the server 106, the server 110, and the server 112 can include one or more engines. Any of the server 106, the server 110, and the server 112 can incorporate one or more datastores. Any of the server 106, the server 110, and the server 112 can incorporate components similar to the components shown in the computer system of FIG. 9.

The engines in any of the server 106, the server 110, and the server 112 can be are dedicated in whole or in part to serving the needs or requests of other programs and/or devices. Any of the server 106, the server 110, and the server 112 can handle relatively high processing and/or memory volumes and relatively fast network connections and/or throughput. The server 106, the server 110, and the server 112 may or may not have device interfaces and/or graphical user interfaces (GUIs). In some embodiments, any of the server 106, the server 110, and the server 112 can meet or exceed high availability standards. For instance, the server 106, the server 110, and the server 112 can incorporate robust hardware, hardware redundancy, network clustering technology, or load balancing technologies to ensure availability. In some embodiments, the server 106, the server 110, and the server 112 can incorporate administration engines that from electronic devices such as the desktop computer 102, the laptop computer 104, or the tablet device 114, or other devices access remotely through the network 108.

Any of the server 106, the server 110, and the server 112 can include an operating system that is configured for server functionality, i.e., to provide services relating to the needs or requests of other programs and/or devices. For instance, the operating system in the server 106, the server 110, or the server 112 can include advanced or distributed backup capabilities, advanced or distributed automation modules and/or engines, disaster recovery modules, transparent transfer of information and/or data between various internal storage devices as well as across the network, and advanced system security with the ability to encrypt and protect information regarding data, items stored in memory, and resources. In some embodiments, the server 106, the server 110, and the server 112 can incorporate a version of a Windows® server operating system from Microsoft Corporation, a version of a Mac server operating system from Apple Corporation, a Linux based server operating system, a UNIX based server operating system, a Symbian server operating system, a Blackberry server operating system, or other operating system.

The server 106, the server 110, and the server 112 can distribute functionality and/or data storage. For instance, the server 106, the server 110, and the server 112 can distribute the functionality of an application server and can therefore run different portions of one or more applications concurrently. In such a case, each of the server 106, the server 110, and the server 112 stores and/or executes distributed portions of application services, communication services, database services, web and/or network services, storage services, and/or other services. The server 106, the server 110, and the server 112 can distribute storage of different engines or portions of engines. For instance, any of the server 106, the server 110, and the server 112 can include some or all of the engines shown in the cloud-based server engine 200, shown in FIG. 2.

The networking system 100 can include the network 108. The network 108 can include a networked system that includes several computer systems coupled, such as a local area network (LAN), the Internet, or some other networked system. The term "Internet" as used in this paper refers to a network of networks that uses certain protocols, such as the TCP/IP protocol, and possibly other protocols such as the HTTP for hypertext markup language (HTML) documents that make up the World Wide Web (the web). Content servers, which are "on" the Internet, often provide the content. A web server, which is one type of content server, is typically at least one computer system, which operates as a server computer system, operates with the protocols of the World Wide Web, and has a connection to the Internet. Applicable known or convenient physical connections of the Internet and the protocols and communication procedures of the Internet and the web are and/or can be used. The network 108 can broadly include, as understood from relevant context, anything from a minimalist coupling of the components illustrated in the example of FIG. 1, to every component of the Internet and networks coupled to the Internet. However, components that are outside of the control of the networking system 100 are sources of data received in an applicable known or convenient manner.

The network 108 can use wired or wireless technologies, alone or in combination, to connect the devices inside the networking system 100. Wired technologies connect devices using a physical cable such as an Ethernet cable, digital signal link lines (T1-T3 lines), or other network cable. In some embodiments, the private network group 120 can comprise a wired local area network wired personal area network (PAN), a wired LAN, a wired metropolitan area network, or a wired wide area network. Some or all of the network 108 can comprise cables that facilitate transmission of electrical, optical, or other wired signals.

Some or all of the network 108 can also employ wireless network technologies that use electromagnetic waves at frequencies such as radio frequencies (RF) or microwave frequencies. In embodiments, the network 108 can comprise transmitters, receivers, base stations, and other equipment that facilitates communication via electromagnetic waves. Some or all of the network 108 can comprise a wireless personal area network (WPAN) technology, a wireless local area network (WLAN) technology, a wireless metropolitan area network technology, or a wireless wide area network technology. The network 108 can use Global System for Mobile Communications (GSM) technologies, personal communications service (PCS) technologies, third generation (3G) wireless network technologies, or fourth generation (4G) network technologies. The network 108 can also comprise all or portions of a Wireless Fidelity (Wi-Fi) network, a Worldwide Interoperability for Microwave Access (WiMAX) network, or other wireless network.

The networking system 100 can include the private network group 120. The private network group 120 is a group of computers that form a subset of the larger network 108. The private network group 120 can include the laptop computer 122, the desktop computer 124, the scanner 126, the tablet device 128, the access gateway 132, the first physical device 134, the second physical device 136, and the third physical device 138. The laptop computer 122 can be similar to the laptop computer 104, the desktop computer 124 can be similar to the desktop computer 102, and the tablet device 128 can be similar to the tablet device 114. Any of the laptop computer 122, the desktop computer 124, the scanner 126, the tablet device 128, the access gateway 132, the first physical device 134, the second physical device 136, and the third physical device 138 can include computer systems, engines, datastores. Any of the laptop computer 122, the desktop computer 124, the scanner 126, the tablet device 128, the access gateway 132, the first physical device 134, the second physical device 136, and the third physical device 138 can incorporate components similar to the components in the networking system of FIG. 8.

In some embodiments, the private network group 120 can include a private network. A private network provides a set of private internet protocol (IP) addresses to each of its members while maintaining a connection to a larger network, here the network 108. To this end, the members of the private network group 120 (i.e., the laptop computer 122, the desktop computer 124, the scanner 126, the tablet device 128, the first physical device 134, the second physical device 136, and the third physical device 138) can each be assigned a private IP address irrespective of the public IP address of the router 132.

Though the term "private" appears in conjunction with the name of the private network group 120, in some embodiments, the private network group 120 can actually comprise a public network that forms a subset of the network 108. In such a case, each of the laptop computer 122, the desktop computer 124, the scanner 126, the tablet device 128, the first physical device 134, the second physical device 136, and the third physical device 138 can have a public IP address and can maintain a connection to the network 120. In some embodiments, the connection of some or all of the laptop computer 122, the desktop computer 124, the scanner 126, the tablet device 128, the first physical device 134, the second physical device 136, and the third physical device 138 can be a wired or a wireless connection.

The private network group 120 can comprise the access gateway 132. In some embodiments, the access gateway 132 assigns private IP addresses to each of the devices 122, 124, 126, 128, 134, 136, and 138. The access gateway 132 can establish user accounts for each of the devices 122, 124, 126, 128, 134, 136, and 138 and can restrict access to the network 108 based on parameters of those user accounts. The access gateway 132 can also function as an intermediary to provide content from the network 108 to the devices 122, 124, 126, 128, 134, 136, and 138. For instance, the access gateway 132 can format and appropriately forward data packets traveling over the network 108 to and from the devices 122, 124, 126, 128, 134, 136, and 138. In some embodiments, the access gateway 132 can be a router, a bridge, or other access device. The access gateway 132 can maintain a firewall to control communications coming into the private network group 120 through the network 108.

The access gateway 132 can also control public IP addresses associated with each of the laptop computer 122, the desktop computer 124, the scanner 126, the tablet device 128, the first physical device 134, the second physical device 136, and the third physical device 138. In some embodiments, the access gateway 132 is absent and each of the devices inside the private network group 120 can maintain its own connection to the network 108. The desktop computer 124 is shown connected to the access gateway 132 as such a configuration is a common implementation. However, the functions described in relation to the desktop computer 124 can be implemented on the laptop computer 122, the tablet device 128, or any applicable computing device.

The private network group 120 can be located inside a common geographical area or region. The private network group 120 can be located, for example, in a school, a residence, a business, a campus, or other location. In some embodiments, the private network group 120 is located inside a health office, such as the office of a dentist, a doctor, a chiropractor, a psychologist, a veterinarian, a dietician, a wellness specialist, or other health professional.

The physical devices 134, 136, and 138 can image a physical object. The physical devices 134, 136, and 138 can connect to the desktop computer 124 via a network connection or an output port of the desktop computer 124. Similarly, the physical devices 134, 136, and 138 can connect to the laptop computer 122, the tablet device 128, or a mobile phone. In some embodiments, the physical devices 134, 136, and 138 are directly connected to the access gateway 132. The physical devices 134, 136, and 138 can also internally incorporate network adapters that allow a direct connection to the network 108.

In some embodiments, the first physical device 134 can be a sensor-based imaging technology. A sensor is a device with electronic, mechanical, or other components that measures a quantity from the physical world and translates the quantity into a data structure or signal that a computer, machine, or other instrument can read. The first physical device 134 can use a sensor to sense an attribute of a physical object. The physical object can include, for instance, portions of a person's mouth, head, neck, limb, or other body part. The physical object can be an animate or inanimate item.

In some embodiments, the sensor can comprise X-ray sensors to determine the boundaries of uniformly or non-uniformly composed material such as part of the human body. The sensor can be part of a Flat Panel Detector (FPD). Such an FPD can be an indirect FPD comprising amorphous silicon or other similar material used along with a scintillator. The indirect FPD can allow the conversion of X-ray energy to light, which is eventually translated into a digital signal. Thin Film Transistors (TFTs) or Charge Coupled Devices (CCDs) can subsequently allow imaging of the converted signal. Such an FPD can also be a direct FPD that uses Amorphous Selenium or other similar material. The direct FPD can allow for the direct conversion of X-ray photons to charge patterns that, in turn, are converted to images by an array such as a TFT array, an Active Matrix Array, or by Electrometer Probes and/or Microplasma Line Addressing. The sensor can also comprise a High Density Line Scan Solid State detector.

The sensor of the first physical device 134 can comprise an oral sensor. An oral sensor is a sensor that a user such as a health practitioner can insert into a patient's mouth. For instance, the first physical device 134 can reside in a dentist's office that operates the private network group 120. The sensor of the first physical device 134 can also comprise a sensor that is inserted into a person's ear, nose, throat, or other part of a person's body.

The second physical device 136 can comprise a digital radiography device. Radiography uses X-rays to view the boundaries of uniformly or non-uniformly composed material such as part of the human body. Digital radiography is the performance of radiography without the requirements of chemical processing or physical media. Digital radiography allows for the easy conversion of an image to a digital format. The digital radiography device can be located in the office of a health professional.

The third physical device 138 can comprise a thermal-based imaging technology. Thermal imaging technology is technology that detects the presence of radiation the infrared ranges of the electromagnetic spectrum. Thermal imaging technology allows the imaging of the amount of thermal radiation emitted by an object. The third physical device 138 can comprise an oral sensor, or a sensor that is inserted into a person's ear, nose, throat, or other part of a person's body. In some embodiments, the third physical device 138 resides in the office of a health professional, such as the office of a dentist, a doctor, a chiropractor, a psychologist, a veterinarian, a dietician, a wellness specialist, or other health professional.

The foregoing description of the first physical device 134, the second physical device 136, and the third physical device 138 is illustrative. An office can employ one or more of the first physical device 134, the second physical device 136, and the third physical device 138 alone or in combination. Moreover, each of the first physical device 134, the second physical device 136, and the third physical device 138 can reside in a general-purpose computer, such as the desktop computer 124, the tablet device 128, the laptop computer 122, and/or a mobile phone.

The networking system 100 can facilitate delivery of a cloud application imaging service. A cloud application imaging service is a service that allows an entity associated with a physical device (such as one of the physical devices 134, 136, and 138) to use a cloud-computing application that is executed on a client computer (such as the desktop computer 124) to direct the physical device to image a physical object. Cloud-based computing, or cloud computing, is a computing architecture in which a client can execute the full capabilities of an application in a container (such as a web browser). Though the application executes on the client, portions of the application can be distributed at various locations across the network. For instance, portions of the cloud application imaging service that are facilitated by the networking system 100 can reside on one or more of the desktop computer 102, the laptop computer 104, the server 106, the server 110, the server 112, the tablet device 114, and/or other locations "in the cloud" of the networking system 100. The application can appear as a single point of access for an end-user using a client device such as the desktop computer 124.

The cloud application imaging service can implement cloud client functionalities onto the desktop computer 124. A cloud client incorporates hardware and/or software that allows a cloud application to run in a container such as a web browser. Allowing the desktop computer 124 to function as a cloud client requires the presence of a container in which the cloud application imaging service can execute on the desktop computer 124.

The cloud application imaging service can facilitate communication over a cloud application layer between the client engines on the desktop computer 124 and the one or more server engines on the desktop computer 102, the laptop computer 104, the server 106, the server 110, the server 112, the tablet device 114, and/or other locations "in the cloud" of the networking system 100. The cloud application layer or "Software as a Service" (SaaS) facilitates the transfer over the Internet of software as a service that a container, such as a web browser, can access. Thus, as discussed above, the desktop computer 124 need not install the cloud application imaging service even though the cloud application imaging service executes on the desktop computer 124.

The cloud application imaging service can also deliver to the desktop computer 124 one or more Cloud Platform as a Service (PaaS) platforms that provide computing platforms, solution stacks, and other similar hardware and software platforms. Moreover, the cloud application imaging service can deliver cloud infrastructure services, such as Infrastructure as a Service (IaaS) that can virtualize and/or emulate various platforms, provide storage, and provide networking capabilities. Accordingly, the cloud application imaging service, consistent with cloud-computing services in general, allows users of the desktop computer 124 to subscribe to specific resources that are desirable for imaging and other tasks related to the physical devices 134, 136, and 138. Providers of the cloud application imaging service can bill end-users on a utility computing basis, and can bill for use of resources. In the health context, providers of the cloud application imaging service can bill for items such as the number of images an office wishes to process, specific image filters that an office wishes to use, and other use-related factors.

Figure 2:
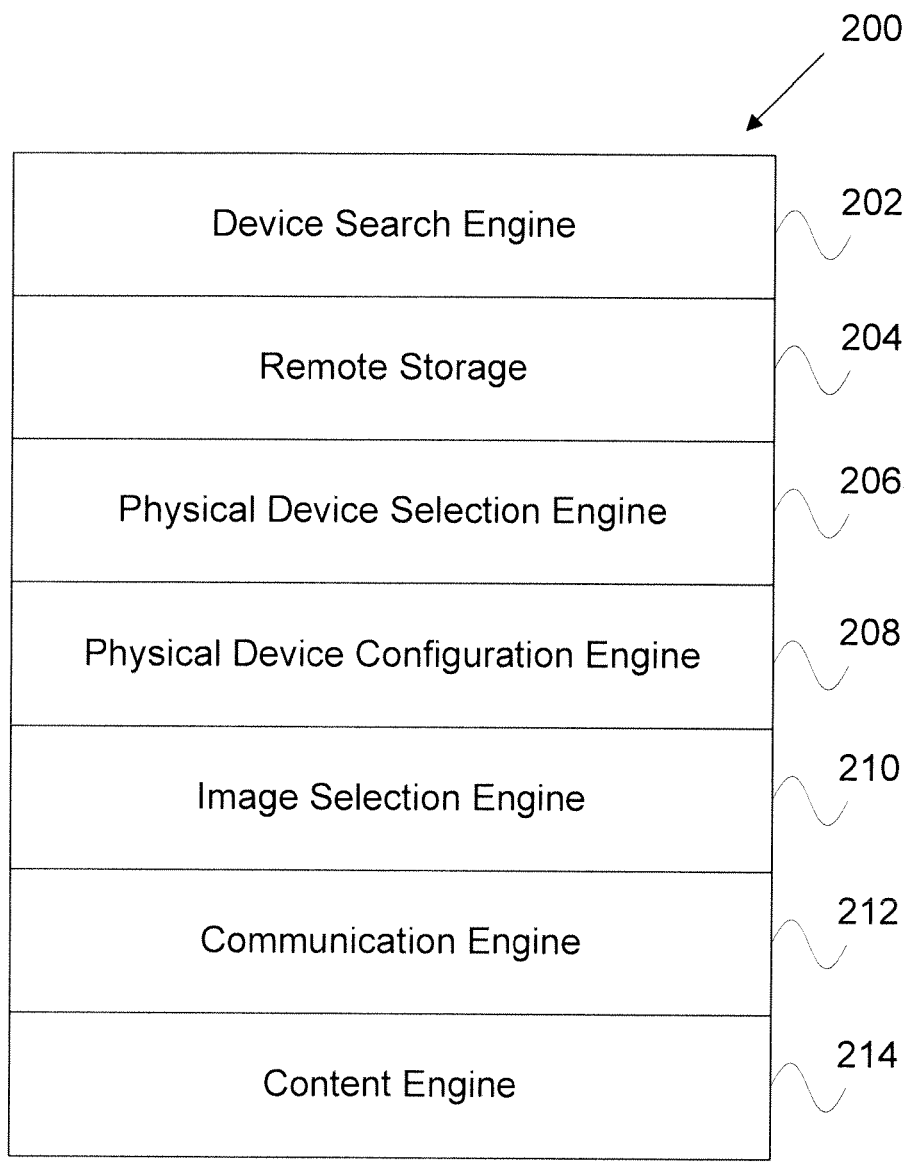
FIG. 2 shows a conceptual diagram of an example of a cloud-based server engine.

As discussed, part or all of the cloud application imaging service can reside on one or more server engines. FIG. 2 shows a conceptual diagram of an example of a cloud-based server engine 200. The cloud-based server engine 200 can comprise a device search engine 202 that searches the physical devices connected to a client computer. The cloud-based server engine 200 can also comprise remote storage 204 that comprises one or more datastores and/or memory units. The remote storage 204 can include storage on Apache-based servers that are available on a cloud platform such as the EC2 cloud platform made available by Amazon.

Further, the cloud-based server engine 200 can comprise a physical device selection engine 206 that selects a specific physical device connected to a client. The cloud-based server engine 200 can include a physical device configuration engine 208 that configures image parameters and/or attributes of the specific physical device. An image selection engine 210 inside the cloud-based server engine 200 can allow the selection of a specific image from the physical device. A communication engine 212 inside the cloud-based server engine 200 allow the transfer of selection data, parameter data, device data, image data, and other data over a network such as the network 108 shown in FIG. 1. The cloud-based server engine 200 further comprises a content engine 214 that makes images available to client devices associated with a cloud application imaging service.

Processors can control any or all of the components of the cloud-based server engine 200 and these components can interface with datastores. Any or all of the cloud-based server engine 200 can reside on a computing device such as the desktop computer 102, the laptop 104, the tablet device 114, the server 106, the server 110, and/or server 112 of FIG. 1. Portions of the cloud-based server engine 200 can also be distributed across multiple electronic devices, including multiple servers and computers. The discussion accompanying FIG. 6 further addresses the functionality of the cloud-based server engine 200.

Figure 3:
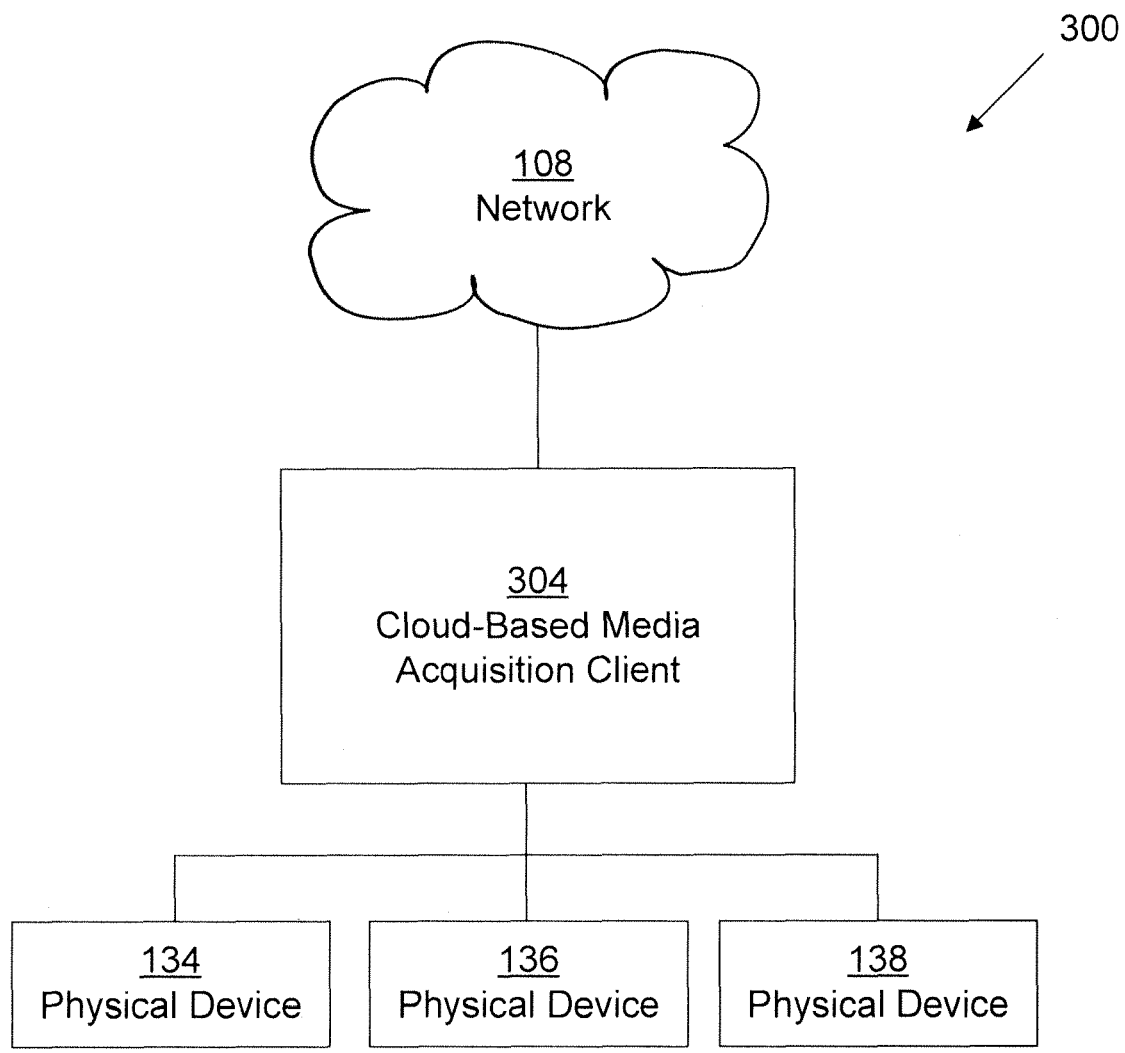
FIG. 3 shows a conceptual diagram of an example of a cloud-based client system.

FIG. 3 shows a conceptual diagram of an example of a cloud-based client system 300. The cloud-based client system 300 can include the network 108, the first physical device 134, the second physical device 136, and the third physical device 138. Each of the network 108, the first physical device 134, the second physical device 136, and the third physical device 138 can take a form similar to its counterpart in FIG. 1.

The cloud-based client system 300 can also include a cloud-based media acquisition client 304. The cloud-based media acquisition client 304 can reside inside a computer, such as the desktop computer 124 in FIG. 1. The cloud-based media acquisition client 304 also interfaces with the network 108. In some embodiments, the access gateway 132 (in FIG. 1) allows the cloud-based media acquisition client 304 to communicate with the network 108. The cloud-based media acquisition client 304 can also be connected to the network 108 through other I/O devices and/or means. As shown in FIG. 2, the cloud-based media acquisition client 304 is also connected to the first physical device 134, the second physical device 136, and the third physical device 138. Either a network connection or an I/O device and/or means can facilitate the connections between the cloud-based media acquisition client 304 and any of the first physical device 134, the second physical device 136, and the third physical device 138. The discussion accompanying FIG. 7 further addresses the functionality of the cloud-based client system 300.

Figure 4:
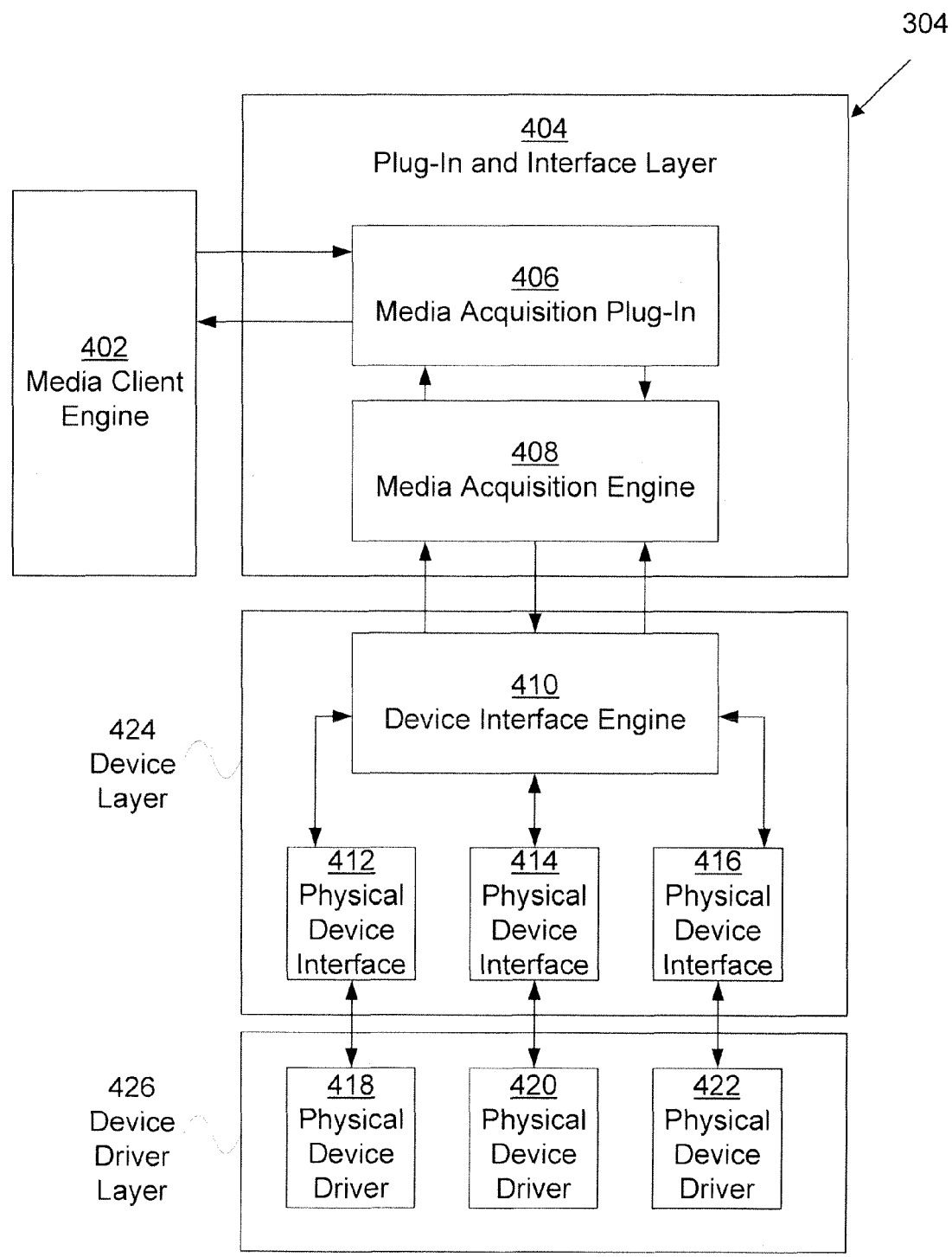
FIG. 4 shows a conceptual diagram of an example of a cloud-based client engine.

FIG. 4 shows a conceptual diagram of the cloud-based client engine 304 in detail. As shown, the cloud-based client engine 304 can comprise a media client engine 402, a plug-in and interface layer 404, a device layer 424, and a device driver layer 426. Any or all of the elements of the cloud-based client engine 304 can reside on a single client, such as the desktop computer 124. The elements of the cloud-based client engine 304 can also be distributed across multiple clients that are located within a single private networking group. For instance, the elements of the cloud-based client engine 304 can be distributed across the laptop computer 122, the desktop computer 124, and the tablet device 128, all within the private networking group 120 in FIG. 1.

The media client engine 402 in the cloud-based client engine 304 can lie in the web application layer of the cloud-based client engine 304. The media client engine 402 can execute portions of a web application such as user interface elements with which users such as health professionals see, use, and interact. In some embodiments, the media client engine 402 can execute portions of code written in PHP and/or scripts such as Javascript. The media client engine 402 can also access portions of a Structured Query Language (SQL) such as a Postgre SQL database stored on one or more cloud servers.

In some embodiments, media client engine 402 can include application-level image filters and/or enhancements. The media client engine 402 can therefore allow a user such as a health professional to adjust factors such as an image's contrast, gamma values, brightness, opacity, and noise. The application-level image filters can also employ custom algorithms and models that are specific to a particular sensor used to obtain an image. Thus, application-level image filters in the media client engine 402 can include specific algorithms for X-ray sensors, thermal sensors, oral sensors, and other sensors. The filtering algorithms available to a specific user such as a specific health care professional can depend on the terms of his or her cloud application imaging service. A specific health care professional can choose to purchase only those application-level filters inside the media client engine 402 that he or she finds of greatest application to his or her practice.

The plug-in and interface layer 404 comprises a media acquisition plug-in 406 and a media acquisition engine 408. The media acquisition plug-in 406 integrates into the media client engine 402 while the media acquisition engine 408 interfaces with lower-level engines, such as the engines inside the device layer 424. The discussion accompanying FIG. 5 further addresses the functionalities of the media acquisition plug-in 406 and the media acquisition engine 408.

The device layer 424 interfaces with the plug-in and interface layer 404 and also abstracts the device driver layer 426 to allow a user of the media client engine 402 to manage physical devices without intimately knowing the device driver's inner workings or functionality. The device layer 424 further incorporates device interface engine 410, a first physical device interface 412, a second physical device interface 414, and a third physical device interface 416. The device interface engine 410 can expose an application-programming interface (API) to the plug-in and interface layer 404. Various programming languages and/or platforms, such as the C++ language, can form the basis of the API in the device layer 424 layer. The API can allow the plug-in and interface layer 404 to communicate with individual device drivers. The device interface engine 410 can create a common, generic class that serves as the foundation for specific hardware devices (such as the first physical device 134, the second physical device 136, and the third physical device 138). The common, generic class created by the device interface engine 410 provides a template that allows higher-level engines, such as engines operating at the plug-in and interface layer 404 and/or the media client engine 402, to initialize devices or get the data of devices.

The device interface engine 410 can also build the functionality unique to each individual hardware device on top of the common, generic device foundation. That is, a specific device (such as one of the first physical device 134, the second physical device 136, and the third physical device 138) corresponding to a particular manufacturer can require a unique sequence of numbers in order to initialize. The device interface engine 410 can also therefore implement specific sequences for particular devices to initialize. Each device implementation communicates with the device drivers available on the user's system and implements the protocols specific to each device. Each device implementation can be packaged into one or more standalone libraries that can be loaded on demand by the device interface engine 410 and thus made available to the user.

The device interface engine 410 can also provide a discovery mechanism that informs the plug-in and interface layer 404 which drivers are installed on the user's system. Users, such as health professionals would therefore be limited from select, on the media acquisition engine 402, a sensor or a physical device to which he or she lacks access.

The first physical device interface 412, the second physical device interface 414, and the third physical device interface 416 translate the commands from the device interface engine 410 to a data structure that is compatible with their respective device drivers. In some embodiments, one or more of the first physical device interface 412, the second physical device interface 414, and the third physical device interface 416 can implement engines and/or modules that translate commands on the level of the APIs in the device interface engine 410 (e.g., C++APIs) to commands that comports with the level of the individual device drivers.

The device driver layer 426 comprises a first physical device driver 418, a second physical device driver 420, and a third physical device driver 422. The device drivers 418, 420, and/or 422 can be written in a variety of languages and can be targeted to specific platforms based on a hardware manufacturer's specifications. The device driver layer 426 can support various commercially available device drivers. The discussion accompanying FIG. 7 further addresses the functionality of the cloud-based client engine 304.

Figure 5:
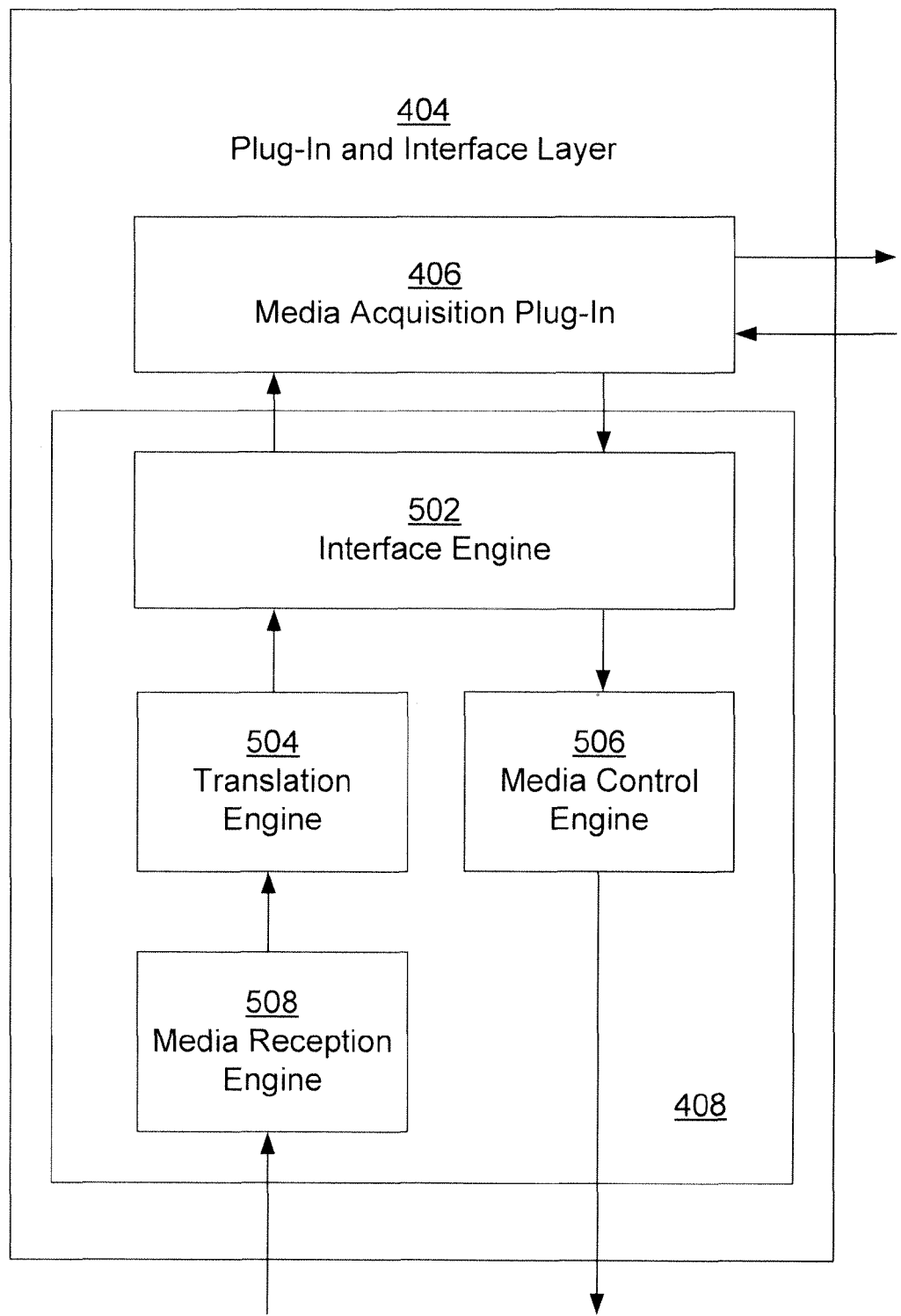
FIG. 5 shows a conceptual diagram of an example of a plug-in and interface layer.

FIG. 5 shows a conceptual diagram of the plug-in and interface layer 404 in detail. The plug-in and interface layer 404 can integrate into a container such as a user's web browser and can allow a web application to access and communicate with the hardware device drivers available on the cloud-based media acquisition client 304. As such, the plug-in and interface layer 404 can integrate into the media client engine 402 to facilitate access to the device drivers of the physical devices.

The plug-in and interface engine 404 can comprise the media acquisition plug-in 406 and the media acquisition engine 408. The media acquisition plug-in 406 can interface with the media client engine 402, shown in FIG. 4. The media acquisition plug-in 406 can expose an API to the applications that the media client engine 402 holds. The media acquisition plug-in 406 can therefore allow the media client engine 402 to receive and transmit information. The information can be encoded to facilitate, for example, object notation, and other encoding parameters.

In some embodiments, the API of the media acquisition plug-in 406 is compatible with a scripting language, such as Javascript. The encoding can comprise a JavaScript Object Notation (JSON) format. Further, in some embodiments, developers can write some or all of the media acquisition plug-in 406 in managed or unmanaged C++ code. The media acquisition plug-in 406 can be compatible with browsers such as Mozilla Firefox, Google Chrome, Microsoft Internet Explorer, and Apple Safari. The media acquisition plug-in 406 therefore acts as an intermediary between the device layer 424 (shown in FIG. 4) and the media client engine 402. The media acquisition plug-in 406 is also responsible for encoding all messages and communication in proper formats.

The media acquisition engine 408 can comprise an interface engine 502, a translation engine 504, a media control engine 506, and a media reception engine 508. The interface engine 502 can include classes that manage device drivers for the physical devices on a high level (i.e., on a level of abstraction that is higher than the level of the device drivers). In some embodiments, the interface engine 502 processes a user selection from the media client engine 402 via the media acquisition plug-in 406. The interface engine 502 can also marshal and/or direct messages between different devices and the media client engine 402 to allow for the initialization of more than a single physical device. In some embodiments, the interface engine 502 facilitates secure transfer of a media item received via the translation engine 504 and the media reception engine 508 to the media client engine 402.

The translation engine 504 can translate a media item to a format compatible with the interface engine 502. The translation engine 504 can also incorporate encryption. In some embodiments, the encryption can be Advanced Encryption Standard (AES) encryption or other encryption standard. The encryption can also have a bit length of 32-bits, 64-bits, 128-bits, 256-bits, 512-bits, or other bit length. The translation engine 504 can also compress received media items. Media item compression is the implementation of algorithms, processes, and/or engines to reduce the irrelevance and/or redundancy of media item data in order to efficiently store or transmit a media item.

The media control engine 506 can direct messages to specific physical devices and their drivers. For instance, the media control engine 506 can select a specific physical device and/or translate configuration parameters of one or more selected physical devices. The media control engine 506 can therefore form an important part of the media acquisition engine 408 by marshalling and/or directing messages and other data.

The media reception engine 508 can receive media items. Received media items can be in a variety of formats. The media reception engine 508 can perform pre-processing steps, such as low-level image filters, to improve the quality of the media item.

The media reception engine 508 can provide a received media item to the translation engine 504. Once encryption and compression are complete, the translation engine 504 securely transfers the image to the remote server. At this point, the image becomes available to the user at the web application layer. In addition, the translation engine 504 can use preliminary image filtering algorithms to ensure the image meets certain quality standards before being transmitted to the remote server. The discussion accompanying FIG. 7 further addresses the functionality of the plug-in and interface layer 404.

Figure 6:
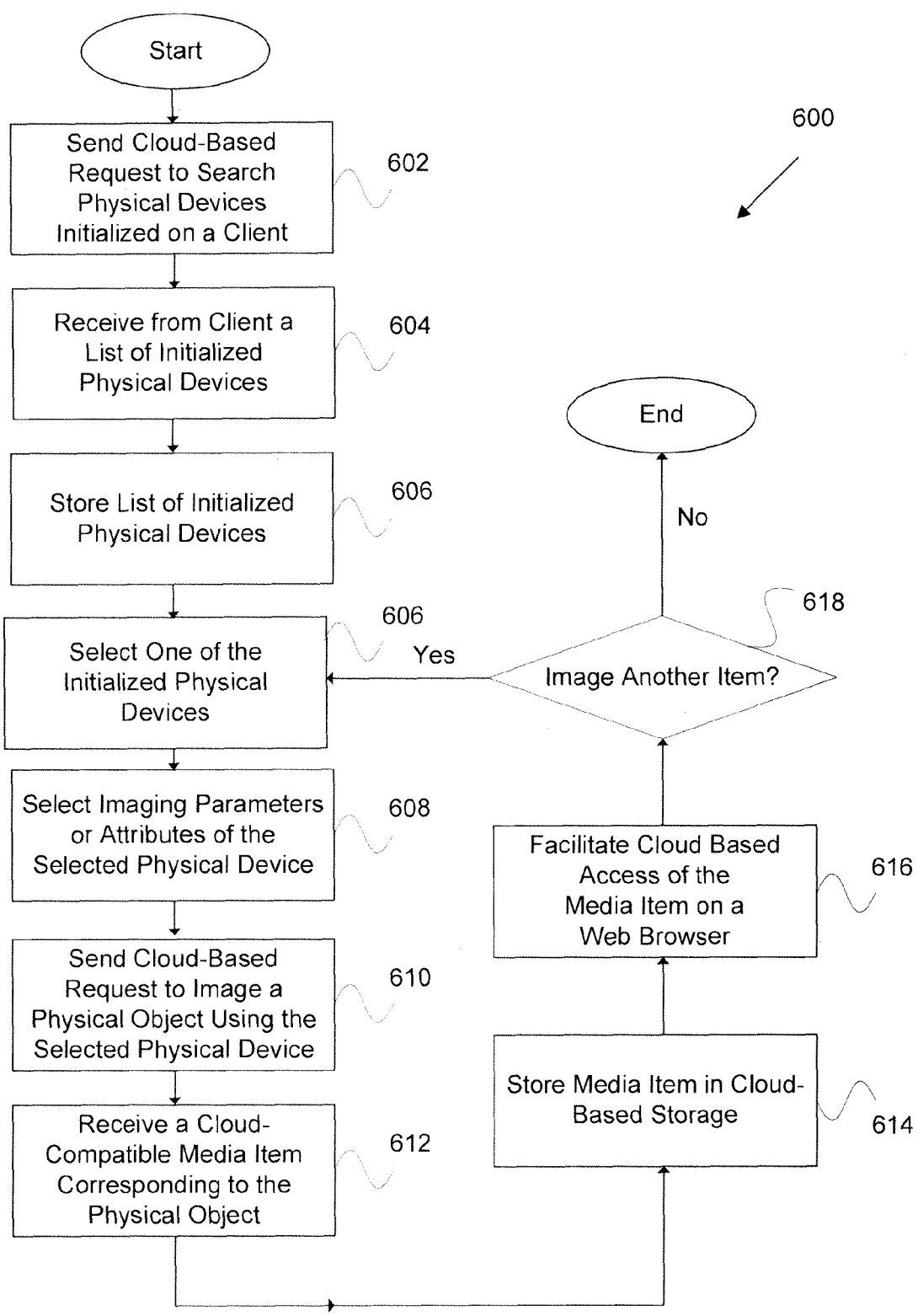
FIG. 6 shows a flowchart of an example of a method for making accessible a cloud-based media item of a physical object.
Figure 7:
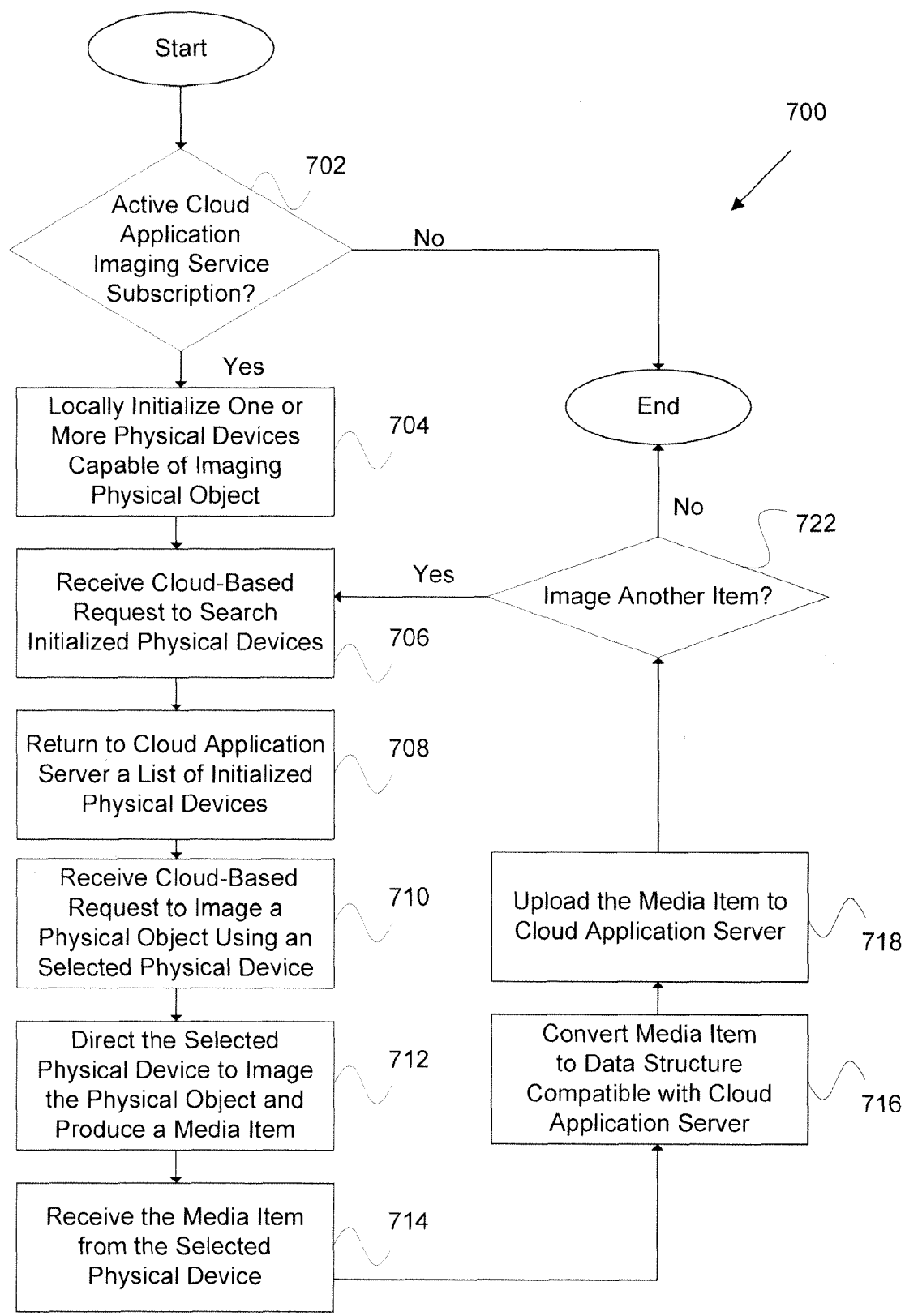
FIG. 7 shows a flowchart of an example of a method for obtaining a cloud-based media item of a physical object.
Figure 8:
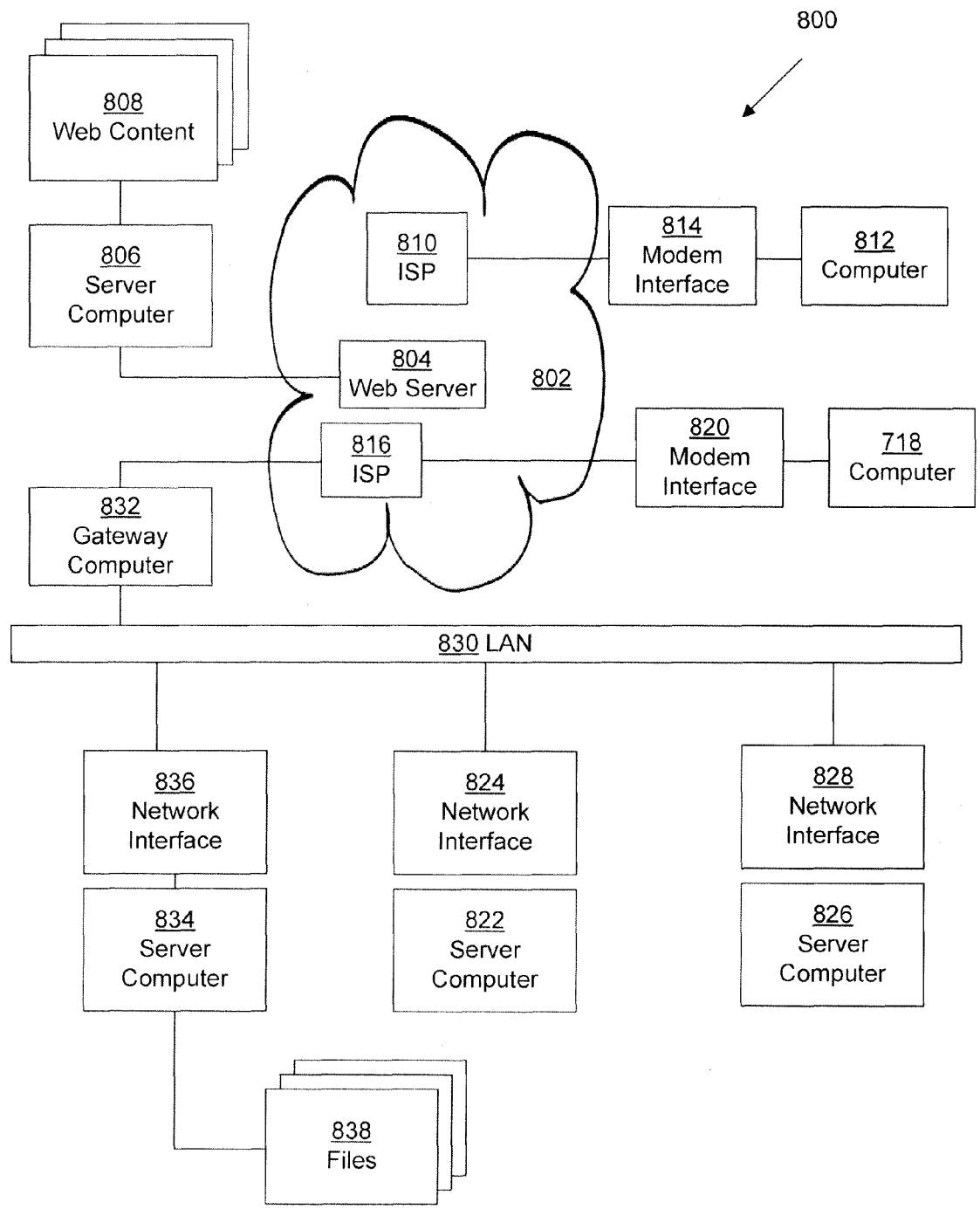
FIG. 8 shows a conceptual diagram of an example of a networking system.

FIGS. 6-8 show methods related to the foregoing structures. One can omit any or all of the steps of the methods in FIGS. 6-8 without departing from the scope and substance of the exemplary inventive concepts disclosed herein. Some steps can also have sub-steps that FIGS. 6-8 do not show.

FIG. 6 shows a flowchart of an example of a method 600 for making accessible a cloud-based media item of a physical object. The discussion of the method 600 refers to the cloud-based server engine 200, shown in FIG. 2.

Step 602 of the flowchart 600 comprises sending a cloud-based request to search one or more physical devices that are initialized on a client. In the cloud-based server engine 200, the device search engine 202 can formulate a query that requests a list of physical devices that are initialized on a client computer. The device search engine 202 can formulate the query and can provide the query to the communication engine 212. The communication engine 212 can format the query as a data packet and can send the packet to a client device. The initialization can occur on the client device and can be similar to step 704, discussed below in the context of FIG. 7.

Step 604 comprises receiving from a client a list of initialized physical devices. The communication engine 212 in FIG. 2 can receive from a client a list of physical devices that are initialized for that client. The communication engine 212 can reformat the list so that the list can be stored. Step 606 comprises storing the list of initialized physical devices. The remote storage 204 in FIG. 2 can store the list of initialized physical devices.

Step 606 comprises selecting one of the initialized physical devices. In FIG. 2, the image device selection engine 206 can obtain the list of initialized physical devices from the remote storage 204. The image device selection engine 206 can filter and/or search through the list to select a single physical device. Step 608 comprises selecting imaging parameters or attributes of the selected physical device. In FIG. 2, the image device configuration engine 208 can select parameters, including size, orientation, brightness, pixel density, data format, and other parameters and/or attributes of images coming from the selected physical device. The image device configuration engine 208 can also provide pre-processing data for the selected physical device.

Step 610 comprises sending a cloud-based request to image a physical object using the selected physical device. In FIG. 2, the image device selection engine 206 and the image device configuration engine 208 can provide their respective data to the communication engine 212. The communication engine 212 can format the data into a packet format to be sent to a cloud-based client.

Step 612 comprises receiving a cloud-based compatible media item corresponding to the physical object. In FIG. 2, the communication engine 212 can receive a cloud-based media item that corresponds to a physical object that the client has imaged. The cloud-based media item can be an image or other media item. The cloud application imaging service can regulate permissions to view and/or modify the cloud-based media item. Step 614 comprises storing the media item in cloud-based storage. After decoding the packet received by the communication engine 212, the cloud-based server engine 200 can store the media item in the remote storage 204.

Step 616 comprises facilitating cloud based access of the media item in a web browser. In FIG. 2, the content engine 214 can make the media item available as part of the cloud application imaging service. As will be discussed below, the media item can be access on a web browser, other container, or as part of a plug-in.

Decision point 618 comprises determining whether to image another item. If another item is to be imaged, the flowchart 600 proceeds to step 606. If another item is not to be imaged, the flowchart 600 terminates.

FIG. 7 shows an example of a flowchart of a method 700 for obtaining a cloud-based media item of a physical object. The discussion of the method 700 refers to the cloud-based client system 300, the cloud-based media acquisition client 304 of FIG. 4, and the plug-in and interface layer 404 of FIG. 5.

Decision point 702 of the flowchart 700 comprises determining whether there is an active cloud application imaging service. If there is no active cloud application imaging service, the flowchart 700 terminates. On the other hand, if there is an active cloud application imaging service, the flowchart 700 proceeds to step 704.

Step 704 comprises locally initializing one or more physical devices capable of imaging a physical object. In FIG. 4, the media acquisition engine 408 can retrieve a list of local devices that network or other physical connections to the cloud-based media acquisition client 304. The media control engine 506 (shown in FIG. 5) inside the media acquisition engine 408 can start a series of initialization protocols that can travel through the device interface layer 410 to the physical device interfaces 412, 414, and 416, and ultimately to the physical device drivers 418, 420, and 422. The initialization protocols can request the respective device drivers to indicate whether these device drivers are active and/or whether respective devices are physically connected. Once device drivers have indicated that they are active and/or physically connected, the media control engine 506 can initialize the physical devices. In some embodiments, the step 704 is executed upon power up or upon the occurrence of a refresh signal from a clock or other indicator.

Step 706 comprises receiving a cloud-based request to search initialized physical devices. The media acquisition engine 408 can receive a request to search initialized physical devices over the network via the media acquisition plug-in 406 and ultimately via the media client engine 402. The request can come from one or more server engines, such as the communication engine 212 in FIG. 2.

Step 708 of the flowchart 700 comprises returning to the cloud application server a list of initialized physical devices. The media acquisition engine 408, through the media reception engine 508, the translation engine 504, and the interface engine 502, can return a list of initialized device physical devices. The media-acquisition plug-in 406 can provide this list to a server engine (such as the server engine 212 in FIG. 2) through the media client engine 402.

Step 710 comprises receiving a cloud-based request to image a physical object using a selected physical device. The interface engine 502 can receive a cloud-based request to image a physical object using one of the physical devices connected to the client. The media acquisition plug-in 406 and/or the media client engine 402 (shown in FIG. 4) can receive such a request. The request can comprise image parameters and/or attributes of the selected physical device.

Step 712 comprises directing the selected physical device to image the physical object and produce the media item. The media control engine 506 (shown in FIG. 5) can direct, through the device interface engine 410 (shown in FIG. 4), the selected physical device to image the physical object. The media control engine 506 (shown in FIG. 5) can also direct, through the device interface engine 410 (shown in FIG. 4), the selected physical device to produce a media item of an image of the physical object. Step 714 comprises receiving the media item from the selected physical device. The media reception engine 508 can receive the media item from the selected physical device.

Step 716 comprises converting the media item to a data structure that is compatible with the cloud server. The translation engine 504 can encode, encrypt, compress, and/or otherwise process the media item so that the media item is compatible with the cloud application imaging service. Step 718 comprises uploading the media item to the cloud application server. The media client engine 402 (in FIG. 4) can upload the media item to a cloud application server through the network to which the media client engine 402 is connected.

Figure 9:
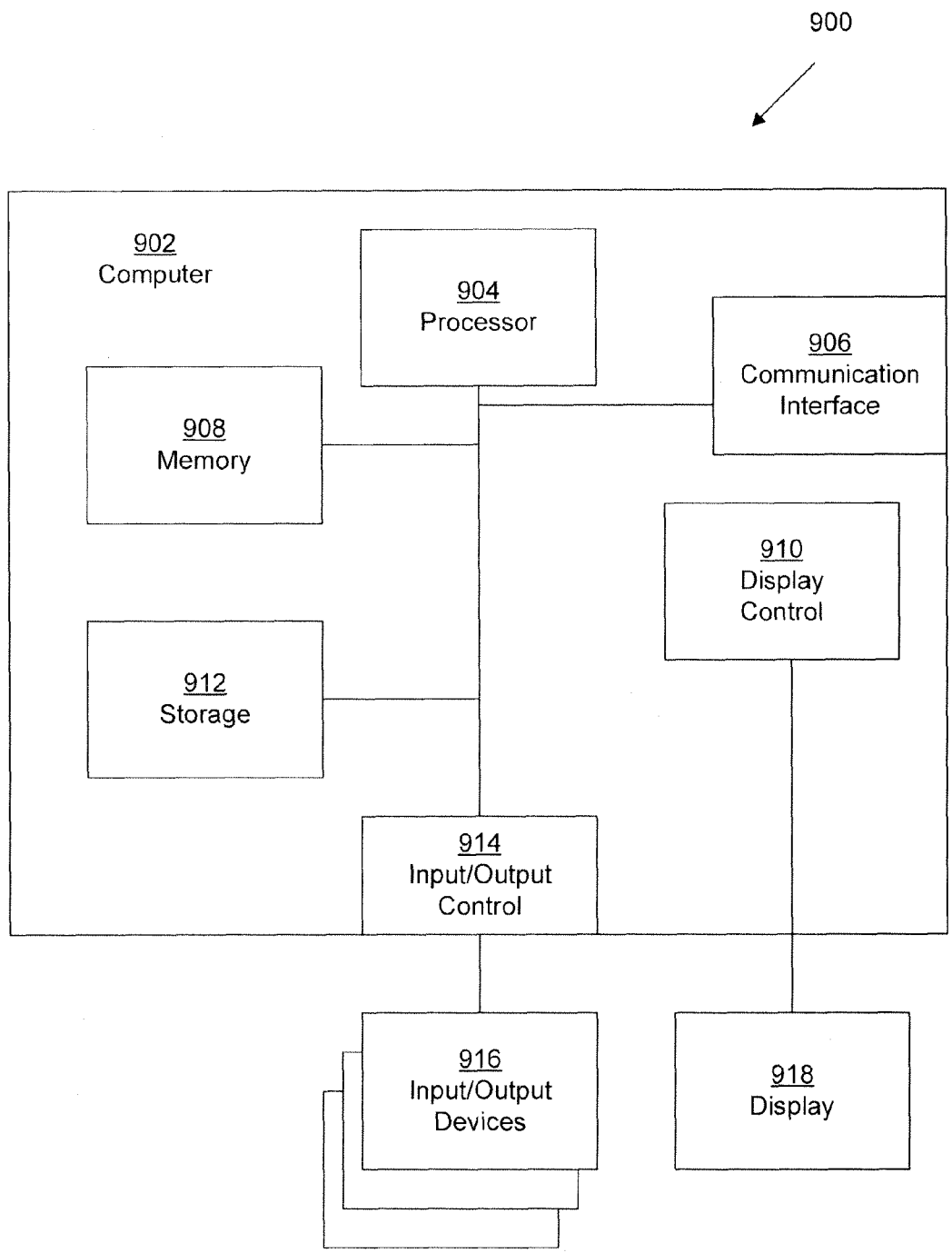
FIG. 9 shows a conceptual diagram of an example of a computer system.

The following description of FIGS. 8 and 9 provides an overview of computer hardware and other operating components suitable for performing the methods of the invention described herein, but does not limit the applicable environments. Similarly, the computer hardware and other operating components can be suitable as part of the apparatuses of the invention described herein. The invention can be practiced with other computer system configurations, including hand-held devices, multiprocessor systems, microprocessor-based or programmable consumer electronics, network PCs, mini-computers, mainframe computers, wireless devices, and the like. The invention can also be practiced in distributed computing environments where tasks are performed by remote processing devices that are linked through a communications network.

FIG. 8 depicts a system on which a distributed management framework for personal attributes can be implemented. FIG. 8 depicts a networked system 800 that includes several computer systems coupled through a network 802, such as the Internet. The term "Internet" as used herein refers to a network of networks which uses certain protocols, such as the TCP/IP protocol, and possibly other protocols such as the hypertext transfer protocol (HTTP) for hypertext markup language (HTML) documents that make up the World Wide Web (the web). The physical connections of the Internet and the protocols and communication procedures of the Internet are well known to those of skill in the art.

The web server 804 is typically at least one computer system that operates as a server computer system and is configured to operate with the protocols of the World Wide Web and is coupled to the Internet. The web server system 804 can be a conventional server computer system. Optionally, the web server 804 can be part of an ISP that provides access to the Internet for client systems. The web server 804 is shown coupled to the server computer system 806 which itself is coupled to web content 808, which can be considered a form of a media database. While two computer systems 804 and 806 are shown in FIG. 8, the web server system 804 and the server computer system 806 can be one computer system having different software components providing the web server functionality and the server functionality provided by the server computer system 806, which will be described further below.

Access to the network 802 is typically provided by Internet service providers (ISPs), such as the ISPs 810 and 816. Users on client systems, such as client computer systems 812, 818, 822, and 826 obtain access to the Internet through the ISPs 810 and 816. Access to the Internet allows users of the client computer systems to exchange information, receive and send emails, and view documents, such as documents that have been prepared in the HTML format.

These documents are often provided by web servers, such as web server 804, which are referred to as being "on" the Internet. Often these web servers are provided by the ISPs, such as ISP 810, although a computer system can be set up and connected to the Internet without that system also being an ISP.

Client computer systems 812, 818, 822, and 826 can each, with the appropriate web browsing software, view HTML pages provided by the web server 804. The ISP 810 provides Internet connectivity to the client computer system 812 through the modem interface 814, which can be considered part of the client computer system 812. The client computer system can be a personal computer system, a network computer, a web TV system, or other computer system. While FIG. 8 shows the modem interface 814 generically as a "modem," the interface can be an analog modem, isdn modem, cable modem, satellite transmission interface (e.g. "direct PC"), or other interface for coupling a computer system to other computer systems.

Similar to the ISP 814, the ISP 816 provides Internet connectivity for client systems 818, 822, and 826, although as shown in FIG. 8, the connections are not the same for these three computer systems. Client computer system 818 is coupled through a modem interface 820 while client computer systems 822 and 826 are part of a LAN 830.

Client computer systems 822 and 826 are coupled to the LAN 830 through network interfaces 824 and 828, which can be Ethernet network or other network interfaces. The LAN 830 is also coupled to a gateway computer system 832 that can provide firewall and other Internet-related services for the local area network. This gateway computer system 832 is coupled to the ISP 816 to provide Internet connectivity to the client computer systems 822 and 826. The gateway computer system 832 can be a conventional server computer system.

Alternatively, a server computer system 834 can be directly coupled to the LAN 830 through a network interface 836 to provide files 838 and other services to the clients 822 and 826, without the need to connect to the Internet through the gateway system 832.

FIG. 9 depicts a computer system 900 for use in the system 800 (FIG. 8). The computer system 900 can be a conventional computer system that can be used as a client computer system or a server computer system or as a web server system. Such a computer system can be used to perform many of the functions of an Internet service provider, such as ISP 810 (FIG. 8).

In the example of FIG. 9, the computer system 900 includes a computer 902, I/O devices 916, and a display device 918. The computer 902 includes a processor 904, a communications interface 910, memory 908, display controller 910, non-volatile storage 912, and I/O controller 914. The computer system 900 can be couple to or include the I/O devices 916 and display device 918.

The computer 902 interfaces to external systems through the communications interface 910, which can include a modem or network interface. It will be appreciated that the communications interface 910 can be considered part of the computer system 900 or a part of the computer 902. The communications interface can be an analog modem, ISDN modem, cable modem, token ring interface, satellite transmission interface (e.g. "direct PC"), or other interfaces for coupling a computer system to other computer systems.

The processor 904 can be, for example, a conventional microprocessor such as an Intel Pentium microprocessor or Motorola power PC microprocessor. The memory 908 is coupled to the processor 904 by a bus 860. The memory 908 can be dynamic random access memory (DRAM) and can include static ram (SRAM). The bus 860 couples the processor 904 to the memory 908, also to the non-volatile storage 912, to the display controller 910, and to the I/O controller 914.

The I/O devices 916 can include a keyboard, disk drives, printers, a scanner, and other input and output devices, including a mouse or other pointing device. The display controller 910 can control in the conventional manner a display on the display device 918, which can be, for example, a cathode ray tube (CRT) or liquid crystal display (LCD). The display controller 910 and the I/O controller 914 can be implemented with conventional well-known technology.

The non-volatile storage 912 is often a magnetic hard disk, an optical disk, or another form of storage for large amounts of data. Some of this data is often written, by a direct memory access process, into memory 908 during execution of software in the computer 902. One of skill in the art will immediately recognize that the terms "machine-readable medium" or "computer-readable medium" includes any type of storage device that is accessible by the processor 904 and encompasses a carrier wave that encodes a data signal.

Objects, methods, inline caches, cache states and other object-oriented components can be stored in the non-volatile storage 912, or written into memory 908 during execution of, for example, an object-oriented software program. In this way, the components illustrated in, for example, FIGS. 1-7 can be instantiated on the computer system 900.

The computer system 900 is one example of many possible computer systems that have different architectures. For example, personal computers based on an Intel microprocessor often have multiple buses, one of which can be an I/O bus for the peripherals and one that directly connects the processor 904 and the memory 908 (often referred to as a memory bus). The buses are connected together through bridge components that perform any necessary translation due to differing bus protocols.

Network computers are another type of computer system that can be used with the present invention. Network computers do not usually include a hard disk or other mass storage, and the executable programs are loaded from a network connection into the memory 908 for execution by the processor 904. A Web TV system, which is known in the art, is also considered to be a computer system according to the present invention, but it can lack some of the features shown in FIG. 9, such as certain input or output devices. A typical computer system will usually include at least a processor, memory, and a bus coupling the memory to the processor.

In addition, the computer system 900 is controlled by operating system software, which includes a file management system, such as a disk operating system, which is part of the operating system software. One example of operating system software with its associated file management system software is the family of operating systems known as Windows® from Microsoft Corporation of Redmond, Wash., and their associated file management systems. Another example of operating system software with its associated file management system software is the Linux operating system and its associated file management system. The file management system is typically stored in the non-volatile storage 912 and causes the processor 904 to execute the various acts required by the operating system to input and output data and to store data in memory, including storing files on the non-volatile storage 912.

While preferred embodiments of the present inventive apparatus and method have been described, it is to be understood that the embodiments described are illustrative only and that the scope of the embodiments of the present inventive apparatus and method is to be defined solely by the appended claims when accorded a full range of equivalence, many variations and modifications naturally occurring to those of skill in the art from a perusal thereof.

The invention claimed is:

1. A media acquisition engine, comprising:
an interface engine that receives a selection from a plug-in coupled to a media client engine, a client associated with the media client engine identified as subscribing to a cloud application imaging service;
a media control engine that directs, in accordance with the selection, one of a plurality of physical devices to image a physical object and produce a media item based on the image of the physical object, the one of the plurality of physical devices coupled to a cloud client;
a media reception engine that receives the media item from the one of a plurality of physical devices;
a translation engine that encodes the media item into a data structure compatible with the cloud application imaging service;
the interface engine configured to transfer the media item to the plug-in.

2. The media acquisition engine of claim 1, wherein the interface engine is configured to transfer the encoded media item to the media client engine.

3. The media acquisition engine of claim 1, wherein the media control engine directs the one of the plurality of physical devices by communicating with a device driver related to the one of the plurality of physical devices.

4. The media acquisition engine of claim 1, wherein the selection corresponds to a user input from a user of the media client engine.

5. The media acquisition engine of claim 1, wherein the selection is part of an automated client-side script executed on the media client engine.

6. The media acquisition engine of claim 1, wherein the translation engine performs an encryption on the media item.

7. The media acquisition engine of claim 6, wherein the encryption comprises a 256-bit Advanced Encryption Standard (AES) encryption.

8. The media acquisition engine of claim 1, wherein the interface engine securely transfers the media item.

9. The media acquisition engine of claim 1, further comprising a media filtering engine that filters the media item, and the interface engine transfers the filtered media item to the plug-in.

10. The media acquisition engine of claim 9, wherein the interface engine restricts the transfer of the filtered media item if the filtered media item does not meet a minimum quality standard.

11. The media acquisition engine of claim 1, wherein the one of the plurality of physical devices comprises a sensor-based imaging technology.

12. The media acquisition engine of claim 11, wherein the sensor-based imaging technology comprises an oral sensor.

13. The media acquisition engine of claim 1, wherein the one of the plurality of physical devices comprises a digital radiography device.

14. The media acquisition engine of claim 1, wherein the one of the plurality of physical devices comprises a thermal-based imaging technology.

15. The media acquisition engine of claim 1, wherein the one of the plurality of physical devices comprises a dental imaging technology.

16. A method comprising:
receiving a selection from a media client engine, a client associated with the media client engine identified as subscribing to a cloud application imaging service;
directing, in accordance with the selection, one of a plurality of physical devices to image a physical object and produce a media item based on the image of the physical object;
receiving the media item from the one of the plurality of physical devices;
encoding the media item into a data structure compatible with the cloud application imaging service;
transferring the encoded media item to the media client engine.

17. The method of claim 16, wherein directing the one of the plurality of physical devices comprises directing a sensor-based imaging device to obtain the image of the physical object.

18. The method of claim 16, wherein encoding the media item comprises encrypting the media item.

19. The method of claim 16, wherein encoding the media item comprises encapsulating the media item into a data packet for transmission on a network.

20. The method of claim 16, wherein the one of the plurality of physical devices comprises a digital radiography device.

* * * * *